US011231357B2

(12) United States Patent
Medvedev

(10) Patent No.: US 11,231,357 B2
(45) Date of Patent: Jan. 25, 2022

(54) SYSTEM AND METHOD FOR OZONE CONCENTRATION IN LIQUIDS HAVING A POSITIVE SCALING FACTOR

(71) Applicant: OWS AGRI LIMITED, London (GB)

(72) Inventor: Dmitry Medvedev, Fort Worth, TX (US)

(73) Assignee: OWS AGRI LIMITED, London (GB)

( * ) Notice: Subject to any disclaimer, the term of this patent is extended or adjusted under 35 U.S.C. 154(b) by 0 days.

(21) Appl. No.: 16/767,312

(22) PCT Filed: Jan. 24, 2018

(86) PCT No.: PCT/US2018/015019
§ 371 (c)(1),
(2) Date: May 27, 2020

(87) PCT Pub. No.: WO2019/147234
PCT Pub. Date: Aug. 1, 2019

(65) Prior Publication Data
US 2020/0408673 A1 Dec. 31, 2020

(51) Int. Cl.
G01N 21/03 (2006.01)
G01N 21/35 (2014.01)
(Continued)

(52) U.S. Cl.
CPC ..... *G01N 21/0303* (2013.01); *G01N 21/3504* (2013.01); *G01N 21/3577* (2013.01);
(Continued)

(58) Field of Classification Search
CPC .......... G01N 21/0303; G01N 21/3504; G01N 21/3577; G01N 21/59; G01N 33/18;
(Continued)

(56) References Cited

U.S. PATENT DOCUMENTS 3,700,468 A 10/1972 Shore et al.
4,507,253 A * 3/1985 Wiesmann ................ C02F 1/78
261/22
(Continued)

FOREIGN PATENT DOCUMENTS

DE 4342624 C1 6/1995

OTHER PUBLICATIONS

International Search Report and Written Opinion for the International Patent Application No. PCT/US2018/015019, dated Apr. 6, 2018, 9 pages.
(Continued)

*Primary Examiner* — Mark R Gaworecki
(74) *Attorney, Agent, or Firm* — Kacvinsky Daisak Bluni PLLC

(57) ABSTRACT

An apparatus includes an emitter comprising an ultraviolet light emitting diode (UV-LED) disposed on a first end of an optical cuvette. An extraction cuvette may hold a liquid having a positive Langelier saturation index (LSI), and having a quantity of ozone gas dissolved therein. Air may be bubbled through the liquid in the extraction cuvette, and may then be directed to the optical cuvette. A detector comprising an ultraviolet light sensor (UV sensor) can be disposed on a second end of the optical cuvette. The UV-LED may be a point source, and the emitter may generate a parallel beam of light. A concentration of ozone in the gas in the optical cuvette can be determined based on a diminution of the UV light beam passing therethrough. This concentration can then be used to determine an ozone concentration in the liquid contained in the extraction cuvette.

18 Claims, 5 Drawing Sheets

(51) Int. Cl.
    *G01N 21/59* (2006.01)
    *G01N 33/18* (2006.01)
    *G01N 21/3504* (2014.01)
    *G01N 21/3577* (2014.01)
    *C01B 13/00* (2006.01)

(52) U.S. Cl.
    CPC ............. *G01N 21/59* (2013.01); *G01N 33/18* (2013.01); *C01B 13/00* (2013.01); *G01N 2021/0389* (2013.01); *G01N 2201/062* (2013.01)

(58) Field of Classification Search
    CPC ..... G01N 2021/0389; G01N 2201/062; G01N 21/01; G01N 21/03; G01N 21/17; C01B 13/00; C01B 13/10
    See application file for complete search history.

(56) References Cited

U.S. PATENT DOCUMENTS

| | | | |
|---|---|---|---|
| 4,549,477 A | 10/1985 | McCabe | |
| 4,732,480 A | 3/1988 | Fortunato et al. | |
| 5,334,355 A | 8/1994 | Faddis | |
| 5,420,432 A | 5/1995 | Manook et al. | |
| 5,632,333 A | 5/1997 | Imamura et al. | |
| 5,868,999 A | 2/1999 | Karlson | |
| 5,972,714 A | 10/1999 | Roland et al. | |
| 6,171,625 B1 | 1/2001 | Denvir et al. | |
| 6,485,769 B2 | 11/2002 | Audy et al. | |
| 6,518,574 B1* | 2/2003 | Castleman | G08B 17/12 250/339.05 |
| 6,673,248 B2 | 1/2004 | Chowdhury | |
| 6,764,659 B2 | 7/2004 | Perlov et al. | |
| 7,375,348 B1 | 5/2008 | Sickenberger et al. | |
| 8,298,418 B2* | 10/2012 | Liechti | B01F 3/04248 210/220 |
| 8,537,352 B2 | 9/2013 | Eikelmann et al. | |
| 2001/0042843 A1* | 11/2001 | Cox | G01N 33/0039 250/504 R |
| 2003/0030011 A1 | 2/2003 | Brown et al. | |
| 2004/0018630 A1 | 1/2004 | Birks et al. | |
| 2004/0052702 A1 | 3/2004 | Shuman et al. | |
| 2004/0097021 A1 | 5/2004 | Augusto et al. | |
| 2004/0241868 A1* | 12/2004 | Cox | G01N 33/0039 436/116 |
| 2005/0103723 A1 | 5/2005 | Wilkins et al. | |
| 2005/0160791 A1* | 7/2005 | Kung | G01N 21/05 73/24.02 |
| 2006/0240558 A1* | 10/2006 | Zhao | G01N 27/305 436/62 |
| 2008/0116054 A1* | 5/2008 | Leach | B01D 53/72 204/157.3 |
| 2008/0304048 A1 | 12/2008 | Tormod | |
| 2009/0120473 A1 | 5/2009 | Lynn | |
| 2010/0027016 A1 | 2/2010 | Birks et al. | |
| 2010/0061885 A1 | 3/2010 | Harley | |
| 2010/0159601 A1* | 6/2010 | Patton | G01N 35/08 436/43 |
| 2010/0212406 A1* | 8/2010 | Browne | B01D 19/0036 73/61.41 |
| 2011/0147580 A1* | 6/2011 | Bell | H01J 49/0431 250/282 |
| 2011/0164245 A1* | 7/2011 | Eikelmann | B01L 9/52 356/246 |
| 2011/0201123 A1 | 8/2011 | Watson et al. | |
| 2012/0006098 A1 | 1/2012 | Degner et al. | |
| 2012/0135396 A1 | 5/2012 | McDevitt et al. | |
| 2013/0045496 A1* | 2/2013 | Jansen | C12Q 1/689 435/8 |
| 2013/0270429 A1 | 10/2013 | Bilenko et al. | |
| 2013/0292581 A1* | 11/2013 | Russell | H01J 49/167 250/423 R |
| 2014/0034840 A1* | 2/2014 | Davenport | G01N 21/33 250/370.01 |
| 2014/0106463 A1* | 4/2014 | Wald | G01N 31/227 436/110 |
| 2015/0070889 A1* | 3/2015 | Sooferian | F21V 17/06 362/232 |
| 2015/0362426 A1 | 12/2015 | Nishino et al. | |
| 2015/0377772 A1 | 12/2015 | Birks et al. | |
| 2016/0103089 A1 | 4/2016 | Boyette et al. | |
| 2016/0187214 A1* | 6/2016 | Al-Hemyari | G01N 33/0016 73/31.04 |
| 2017/0115272 A1* | 4/2017 | Rihani | G01N 21/6486 |
| 2017/0219479 A1 | 8/2017 | Bilenko et al. | |
| 2019/0056317 A1* | 2/2019 | Clausen | G01N 21/33 |

OTHER PUBLICATIONS

International Search Report and Written Opinion for the International Patent Application No. PCT/US18/13797, dated May 10, 2018, 7 pages.
International Search Report and Written Opinion for the International Patent Application No. PCT/US18/14768, dated Apr. 5, 2018, 8 pages.
Nikoleav et al., "Atmospheric Ozone Concentration Measurement by UV Light-Emitting Diode Radiation Absorption" Bulletin of the Lebedev Physics Insitute. 2013, vol. 40 (2), pp. 50-53.
International Search Report and Written Opinion for the International Patent Application No. PCT/US18/14841, dated Mar. 29, 2018, 8 pages.
International Search Report and Written Opinion for the International Patent Application No. PCT/US18/15846, dated Mar. 29, 2018, 9 pages.
International Search Report and Written Opinion for the International Patent Application No. PCT/US18/17601, dated May 7, 2018, 7 pages.

* cited by examiner

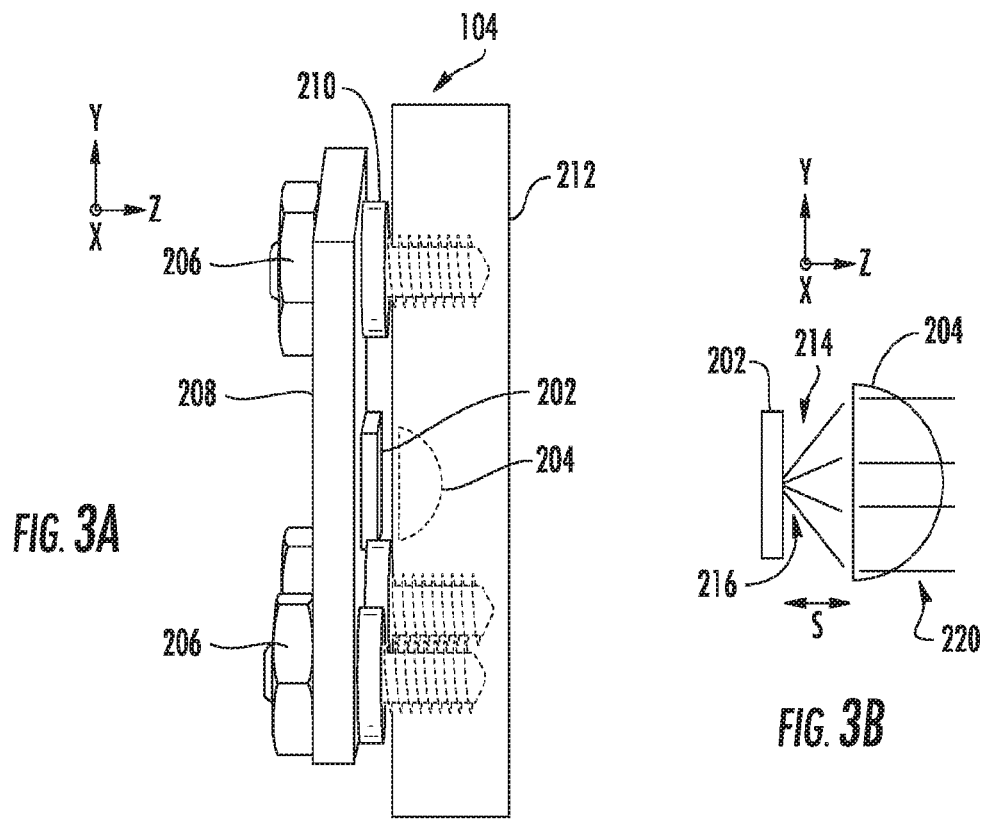
FIG. 3A
FIG. 3B
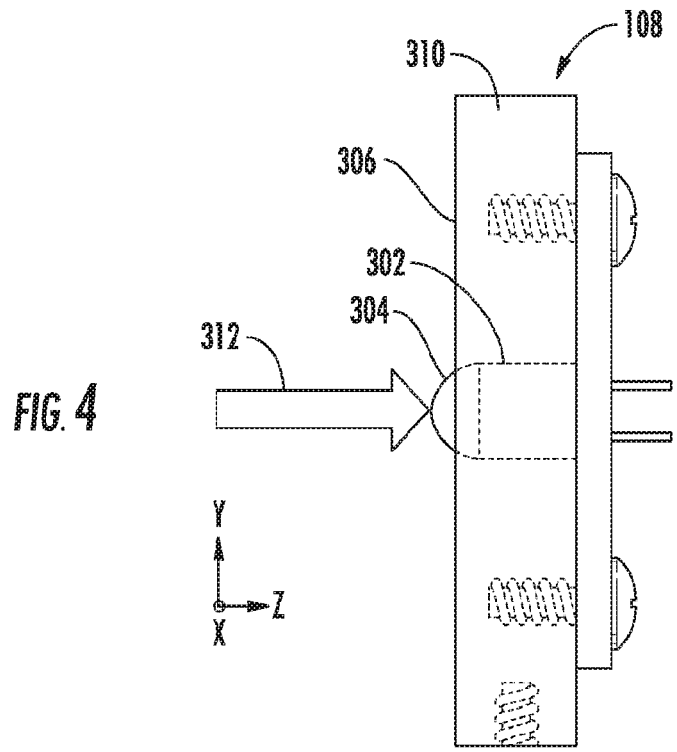
FIG. 4

SYSTEM AND METHOD FOR OZONE CONCENTRATION IN LIQUIDS HAVING A POSITIVE SCALING FACTOR

This is a national stage application filed under 35 U.S.C. § 371 of pending international application PCT/US2018/015019, filed Jan. 24, 2018, the entirety of which application is hereby incorporated by reference herein.

FIELD

The present embodiments relate to gas analyzer devices, more particularly, to gas concentration optical measurement apparatus for use in measuring ozone concentrations in liquids having a positive scaling index, or Langelier Saturation Index (LSI).

BACKGROUND

Gas concentration measurement devices are useful to detect various types of gases including ozone. One type of device takes advantage of the optical absorption of light that may pass through a sample of air or other ambient gas being measured. Ozone is known to strongly absorb light in the short wavelength ultra-violet region of the spectrum, sometimes referred to as UV-C radiation. By placing a source of UV-C radiation at a known distance from a UV-C radiation sensor the concentration of ozone may be determined by measuring the radiation loss and using known optical formula that calculate the absorption or loss of radiation between source and detector for a given concentration of ozone.

Known systems may not be optimized to conveniently and rapidly measure low ozone concentrations. Additionally, measuring the ozone concentration over a wide range of concentrations using the same device may be useful. With respect to these and other considerations, the present disclosure is provided.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

An apparatus is disclosed, including an extraction cuvette having a liquid inlet and a liquid outlet and a gas inlet and a gas outlet, and an optical cuvette having a gas inlet and a gas outlet. The gas inlet of the optical cuvette can be coupled to the gas outlet of the extraction cuvette. The apparatus may further include an emitter comprising an ultraviolet light emitting diode (UV-LED) and a convex lens such that the UV-LED is at a focus of the convex lens. The emitter can be positionable on a first end of the optical cuvette. The optical cuvette may be configured to contain the gas received from the extraction cuvette. The apparatus may also include a detector comprising an ultraviolet light sensor (UV sensor) and being positionable on a second end of the optical cuvette, the second end being opposite the first end. The UV-LED may be a point source, and the emitter may generate a parallel beam of light.

The UV-LED may comprise an emitter generating radiation in the range of 250 nm to 270 nm. The UV sensor may comprise a solar blind UV photodiode. The emitter may comprise an emitter lens, the emitter lens movably coupled to the UV-LED, wherein a position of the UV-LED is adjustable so as to be disposed at a first focus of the emitter lens. The convex lens may comprise a hemisphere. The detector may comprise a detector lens, the detector lens coupled to the UV sensor, wherein the UV sensor is disposed at a second focus of the detector lens. The detector lens may comprise a convex lens.

The gas inlet of the extraction cuvette may be coupleable to a gas distributor within the extraction cuvette to provide the gas in the form of a plurality of bubbles in a liquid disposed in the extraction cuvette. The apparatus may further include a temperature sensor disposed in or on the extraction cuvette for monitoring a temperature of the liquid within the extraction cuvette. The liquid outlet of the extraction cuvette is disposed in a bottom portion of the extraction cuvette, the liquid outlet being coupled to an output pipe or tube for directing the liquid to a drain connection positioned at a level associated with a water level in the extraction cuvette to thereby maintain a predetermined water level in the extraction cuvette. The emitter and detector may be independently movable with respect to each other so as to align the emitter and detector such that the UV-LED emits the light that can be captured by the detector.

An apparatus is disclosed, comprising an extraction cuvette having a liquid inlet and a liquid outlet and a gas inlet and a gas outlet, and an optical cuvette having a gas inlet and a gas outlet, where the gas inlet is coupled to the gas outlet of the extraction cuvette. The apparatus can also include an emitter, the emitter comprising an ultraviolet light emitting diode (UV-LED) and being disposed on a first end of the optical cuvette. The apparatus may further include a detector, the detector comprising an ultraviolet light sensor (UV sensor) and being disposed on a second end of the optical cuvette, the second end being opposite the first end. An insert holder disposed in the optical cuvette, and at least one optical insert may be provided, where the at least one insert is reversibly fixable to the insert holder, and wherein the at least one insert comprises a UV-transmitting material.

The UV-LED may comprise an emitter generating radiation in the range of 250 nm to 270 nm. The UV sensor may comprise a solar blind UV photodiode. The emitter may comprise an emitter lens, the emitter lens movably coupled to the UV-LED, wherein a position of the UV-LED is adjustable so as to be disposed at a first focus of the emitter lens. The detector may comprise a detector lens, the detector lens coupled to the UV sensor, wherein the UV sensor is disposed at a second focus of the detector lens.

The apparatus may further include a first window disposed on the first end of the optical cuvette; and a second window disposed on the second end of the optical cuvette, the first window and the second window comprising a UV-transmitting material. The optical cuvette may comprise a path length of gas traversed by a beam emitted by the UV-LED between the emitter and the detector, wherein the path length of gas is between 0.2 mm and 1 mm when the at least one insert is affixed to the insert holder.

An apparatus is disclosed, comprising an extraction cuvette having a liquid inlet and a liquid outlet and a gas inlet and a gas outlet, and an optical cuvette having a gas inlet and a gas outlet, the gas inlet coupled to the gas outlet of the extraction cuvette. The apparatus may further include an emitter, the emitter comprising an ultraviolet light emitting diode (UV-LED) and being disposed on a first end of the optical cuvette, and an emitter lens, the emitter lens coupled to the UV-LED, where the UV-LED is disposed at a first focus of the emitter lens. A detector may be provided, including an ultraviolet light sensor (UV sensor) and being disposed on a second end of the optical cuvette, the second end being opposite the first end. A detector lens may be coupled to the UV sensor, wherein the UV sensor is disposed at a second focus of the detector lens. An insert holder can be disposed in the optical cuvette. At least one insert may be reversibly fixable to the insert holder, where the at least one insert comprises a UV-transmitting material.

The gas inlet of the extraction cuvette can be coupleable to a gas distributor within the extraction cuvette to provide the gas in the form of a plurality of bubbles in a liquid disposed in the extraction cuvette. The extraction cuvette can further include a temperature sensor disposed in or on the extraction cuvette for monitoring a temperature of the liquid within the extraction cuvette. The liquid outlet of the extraction cuvette is disposed in a bottom portion of the extraction cuvette, the liquid outlet being coupled to an output pipe or tube for directing the liquid to a drain connection positioned at a level associated with a water level in the extraction cuvette to thereby maintain a predetermined water level in the extraction cuvette.

BRIEF DESCRIPTION OF THE DRAWINGS

FIG. 3A depicts an emitter according to an embodiment of the disclosure;

FIG. 3B depicts details of the geometry of the emitter of FIG. 3A;

FIG. 4 depicts a detector according to an embodiment of the disclosure;

Figures 1A, 1B:
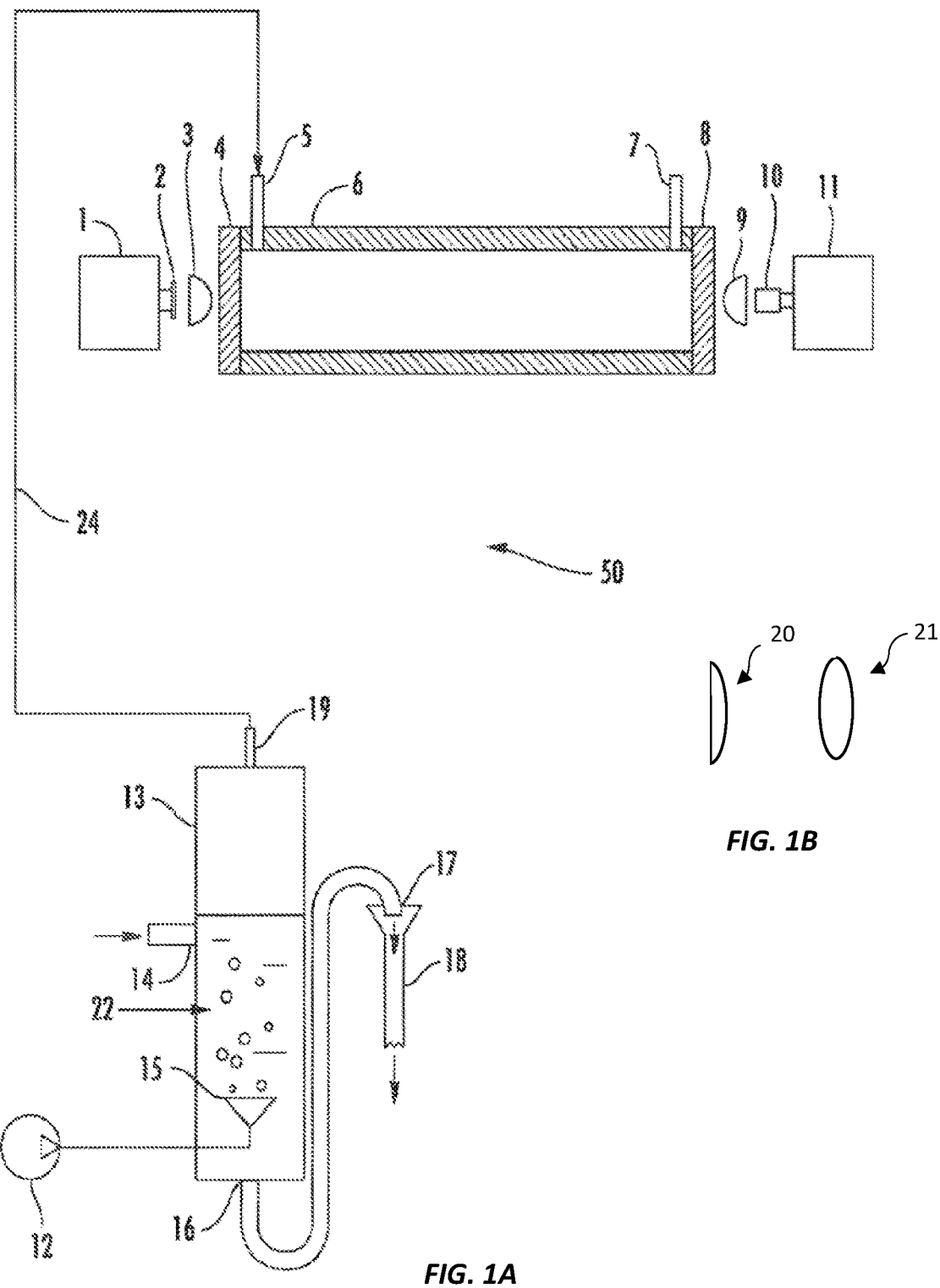
FIG. 1A depicts a schematic view of a system according to the disclosure for determining ozone concentration in a liquid, such as water, having a positive sealing index.
FIG. 1B depicts example convex lens arrangements for use in the system according to FIG. 1A.

The drawings are not necessarily to scale. The drawings are merely representations, not intended to portray specific parameters of the disclosure. The drawings are intended to depict exemplary embodiments of the disclosure, and therefore are not be considered as limiting in scope. In the drawings, like numbering represents like elements.

Furthermore, certain elements in some of the figures may be omitted, or illustrated not-to-scale, for illustrative clarity. The cross-sectional views may be in the form of "slices", or "near-sighted" cross-sectional views, omitting certain background lines otherwise visible in a "true" cross-sectional view, for illustrative clarity. Furthermore, for clarity, some reference numbers may be omitted in certain drawings.

DETAILED DESCRIPTION

The present embodiments will now be described more fully hereinafter with reference to the accompanying drawings, in which some embodiments are shown. The subject matter of the present disclosure, however, may be embodied in many different forms and should not be construed as limited to the embodiments set forth herein. Rather, these embodiments are provided so that this disclosure will be thorough and complete, and will fully convey the scope of the subject matter to those skilled in the art. In the drawings, like numbers refer to like elements throughout.

In various embodiments improved gas concentration measurement apparatus and techniques are presented. The present embodiments may be usefully employed for detection of gas concentrations for UV-absorbing gases, such as ozone. The present embodiments may, be useful in measuring ozone concentrations in liquids having a positive scaling index, or positive Langelier Saturation Index (LSI). Example non-limiting embodiments are related to optically transparent apparatus containing a gas, sometimes referred to as a cuvette. A cuvette may be generally optically transparent and may enclose a contained atmosphere, such as a gas that is deliberately introduced into the cuvette. As detailed below, by employing an emitter to emit electromagnetic radiation into the cuvette into one end and detecting radiation transmitted out of the cuvette at another end, the gas concentration of a gas species within the cuvette may be measured.

In some embodiments, the gas introduced into the cuvette may, in a previous step, have been passed through a liquid having a positive Langelier saturation index (LSI). By measuring the gas concentration of the gas species within the cuvette, a concentration of gas dissolved in the liquid can be determined.

Referring now to FIG. 1A, a system 50 according to the disclosure is shown for determining the concentration of a gas dissolved in a liquid having a positive LSI. In one non-limiting example embodiment, the gas is ozone and the liquid is water. As will be described in greater detail, to determine a concentration of ozone in water having a positive LSI, ozone is first extracted from the liquid by bubbling a gas (e.g., air) the water. The concentration of ozone in the bubbled gas is then determined, and the resulting concentration can be used to determine a concentration of ozone in the liquid.

The system 50 includes an optical cuvette 6 and an extraction cuvette 13. Water having a positive LSI is introduced into the extraction cuvette 13 via liquid input 14. The liquid input 14 is positioned above a liquid output 16, which in the illustrated embodiment is disposed at a bottom end of the extraction cuvette 13. The water 22 passes from the liquid input 14 to the liquid output 16, and is then directed through an output pipe or tube 17 to an open drain connection 18 that is positioned at a level which close to a desired water level in the extraction cuvette 13. In this manner, a stable desired water level in the extraction cuvette 13 is maintained. The water 22 may be supplied from a pressurized source such as a pump (not shown) or other pressurized water supply, and the flow rate of water 22 into and through the extraction cuvette 13 may be regulated via an appropriate throttle valve (not shown) or directly via a pump, if one is used. A flowmeter (not shown) may be used to monitor the flowrate of water into and through the extraction cuvette 13. In some non-limiting example embodiments, the water temperature may be from about 0-50 degrees Celsius. In some non-limiting example embodiments, the liquid flowrate may be from about 50-500 Liters per hour.

In a lower portion of the extraction cuvette 13, an air distributor 15 is provided. Air from a source of compressed air 12 is directed into the extraction cuvette 13 and through the air distributor 15, which may introduce the air as a plurality of air bubbles into the water in the extraction cuvette. The flow rate of air into and through the extraction cuvette 13 may be regulated via an appropriate throttle valve (not shown) or directly via a pump, if one is used. A flowmeter (not shown) may be used to monitor the flowrate of air into and through the extraction cuvette 13.

The air bubbles may extract ozone from the water 22 in the extraction cuvette 13 as they pass through the water in the extraction cuvette. A gas outlet 19 may be positioned at a top portion of the extraction cuvette 13, and may direct ozone-saturated air to an inlet 5 of the optical cuvette 6 via gas line 24.

A temperature sensor (not shown) may be positioned in or on the extraction cuvette 13 to sense a temperature of the water 22 within the cuvette. In some embodiments the sensed temperature may be employed to determine a saturation characteristic (e.g., Henry constant) which relates to an amount of dissolved gas (e.g., ozone) in the water 22 within the extraction cuvette 13.

As will be described in greater detail later, as the ozone saturated air is passed through the optical cuvette 6, a concentration of ozone in the ozone-saturated air may be determined by passing a light beam comprising collimated rays of UV light through the cuvette and measuring a loss in the light beam intensity as it passes through the cuvette. This loss can can be correlated to ozone concentration in the ozone saturated air.

As shown, the system 50 may include a UV LED power supply 1, an emitter including a UV-LED 2 and an emitter lens 3 disposed at one end of the optical cuvette 6. The emitter lens 3 may collimate the rays of light emitted by the UV-LED 2 into a parallel beam of light having trajectories parallel to the long axis of the optical cuvette 6. A detector composed of a detector lens 9 and a UV sensor 10 may be positioned at an end of the optical cuvette opposite that of the emitter. The detector lens 9 may be disposed to intercept the beam and direct it to the UV sensor 10. An amplifier/microcontroller 114 may take digital readings of UV light signal intensity from the UV sensor 10. The optical cuvette 6 may have first and second windows 4, 8 disposed at opposite ends thereof. The first and second windows 4, 8 may be transparent to UV radiation.

The emitter lens 3 and/or detector lens may, in some embodiments, comprise a convex lens 20, 21 as illustrated in FIG. 1B.

Gas (e.g., ozone saturated air) may be introduced into the optical cuvette 6 via the gas inlet 5 which is disposed at or near one end of the cuvette. A gas outlet 7 is disposed at or near an opposite end of the optical cuvette 6 so that the gas can be conducted through the cuvette. As will be described in greater detail below, as the gas flows through the optical cuvette 6 (from inlet 5 to outlet 7) UV light may be passed through the optical cuvette 6. Thus, the UV-LED 2 may be energized, generating radiation that enters the optical cuvette 6 via the emitter lens 3 and the first window 4 as a parallel UV beam. As the parallel UV beam traverses the cuvette, some photons of the beam may be absorbed by a target gas (not shown) to be measured, such as ozone, due to the optical absorption characteristics of the target gas. By the time the beam reaches the detector, the intensity of the beam may be reduced from a first intensity at the point of entering the cuvette 6, to a second intensity at the point of exiting the cuvette 6, where the second intensity is less than the first intensity.

The system 50 may automatically calculate the concentration of ozone in the air introduced into the optical cuvette 6 in a manner described in greater detail below. In some embodiments, the system 50 automatically calculate ozone concentration in water using the following formula:

$$C \text{ in water} = C \text{ in air} * K \text{ saturation} * K \text{ air/water flow} \quad \text{Eq. (1)},$$

Where "C in water" is ozone concentration in water, "C in air" is ozone concentration in air, "K saturation" is a dimensionless saturation constant depending on water temperature, "K air/water flow" is a dimensionless saturation constant depending on water and air flow. Both dimensionless saturation constants may be stored in lookup tables associated with a program embodying the below-described formulas and methods. As will be appreciated by one of ordinary skill in the art, appropriate values for the aforementioned constants can be obtained from existing literature and/or can be calculated from known formulae and then calibrated by comparison with known ozone concentration values in water.

Figure 2A:
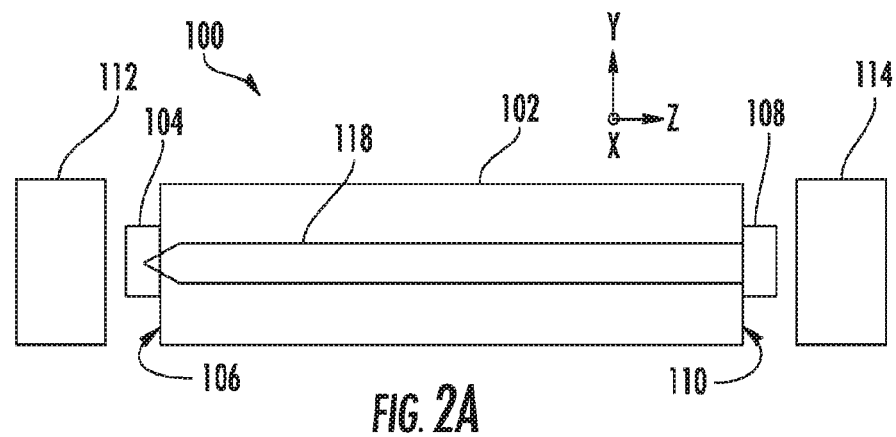
FIG. 2A depicts a side view of a portion of the apparatus according of FIG. 1A.

FIG. 2A depicts an apparatus 100 according to various embodiments of the disclosure. The apparatus 100 may include a bounded volume, such as a chamber 102 (also referred to an optical cuvette), to house a gas. FIG. 2E depicts a perspective view of a variant of the apparatus of FIG. 2A, where the chamber 102 is shaped as a cylinder, although this is not critical and the chamber can assume other shapes. The chamber 102 may be arranged as a cuvette where the chamber 102 has a designed length along the Z-axis of the Cartesian coordinate system shown. The cuvette may have a rectangular cross-section (in the X-Y plane), square cross-section, circular cross-section, or other convenient shape in various non-limiting embodiments. In accordance with various embodiments, the cuvette length (or distance between radiation emitter and sensor) may be in the range of 0.25 centimeters (cm) to a few meters (m) depending on ozone concentration region.

As further shown in FIG. 2A, the apparatus 100 may include an emitter 104 disposed on a first end 106 of the chamber 102, and a detector 108 disposed on a second end 110 of the chamber 102. The emitter 104 may include an ultraviolet (UV) light emitting diode (UV-LED), where the UV-LED is designed to emit radiation having a wavelength arranged according to light absorption characteristics of a target gas or gases to be measured in the chamber 102. In other words, the wavelength or range of wavelengths of radiation emitted by the emitter 104 may be designed to overlap a wavelength or wavelength range where the target gas has a high degree of absorption. In this manner, the presence of a target gas may be detected by the attenuation of electromagnetic radiation directed into the chamber 102 when at least some photons of the radiation are absorbed by the gas.

In embodiments where the apparatus 100 is used as an ozone detector, the emitter 104 may include a UV-LED that emits radiation overlapping in wavelength with an optical absorption peak in ozone centered around 260 nanometers (nm) and having a half-width of approximately 20 nm (see also FIG. 5, discussed below). In particular embodiments, the emitter 104 may include a UV-LED that generates radiation in the range of 250 nm to 300 nm, and more particularly in the range of 250 nm to 270 nm. For example, a known UV LED may be designed to emit radiation over a narrow range, where greater than 75% of the electromagnetic radiation intensity is between 250 nm and 270 nm. This situation ensures that most photons emitted by the emitter 104 will have a wavelength overlapping a wavelength range of the absorption peak for ozone at 260 nm.

Turning now to the detector 108, in various embodiments the detector 108 may include a UV sensor, such as a solar blind UV photodiode. The term "solar blind" may refer to a detector that is not sensitive to solar radiation at the earth's surface, and in particular, may not be sensitive to radiation having wavelengths greater than 290 nm. As is known, the shortest wavelength of UV solar radiation generally incident at the earth's surface is UV-B radiation, whose range is between about 320 nm and 290 nm. Accordingly, the detector 108 may not be sensitive to background electromagnetic radiation (also referred to herein as "light") from the sun during normal operation. This insensitivity to background light facilitates more accurate detection of the concentration of a gas such as ozone, since the radiation being measured at detector 108 may be assumed to be generated from emitter 104.

A hallmark of the apparatus 100 is the configuration of the emitter 104. In particular, the emitter 104 may include various components as detailed below, where the emitter 104 acts as a point source of light. In this manner, radiation generated by the emitter 104 may be manipulated so as to generate a beam 118, composed as a parallel beam, meaning a beam composed of light having light rays that are parallel to one another. Moreover, the beam 118 may be conducted to the detector 108 along a trajectory lying parallel to the long axis of the chamber 102, that is, along the Z-axis. This geometry provides for more efficient generation and detection of the presence and concentration of a gas within the chamber 102 as compared to known ozone detectors. The apparatus 100 may further include a UV-LED power supply 112, arranged according to known power supplies to power the emitter 104, as well as an amplifier/microcontroller 114, coupled to the detector 108. Additionally, the apparatus 100 may include gas conduits (not shown for clarity) to conduct gas into and out of the chamber 102.

Figure 2B:
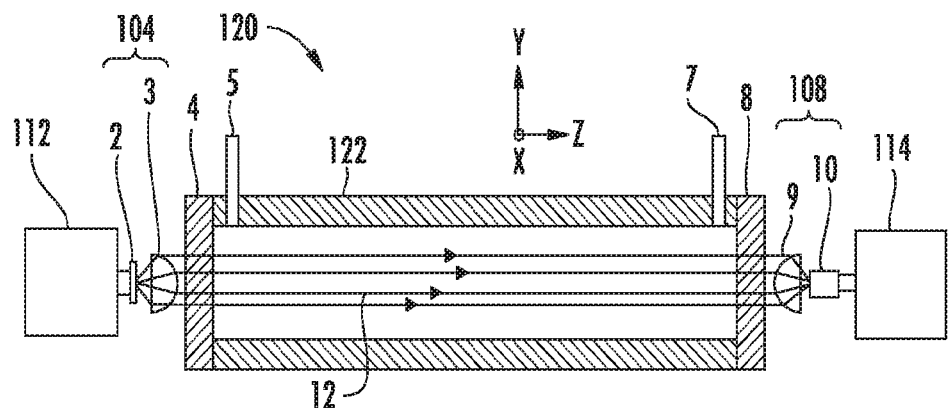
FIG. 2B depicts a side view of another apparatus according to various embodiments of the disclosure.

Turning now to FIG. 2B there is shown an apparatus 120 according to additional embodiments of the disclosure. In this embodiment, the emitter 104 is shown to include a UV-LED 2, whose operation may proceed as generally described above, as well as an emitter lens 3. In accordance with various embodiments of the disclosure, and as discussed in more detail below, the UV-LED 2 may be disposed at a focus of the emitter lens 3, which focus may be deemed a first focus. As suggested in FIG. 2B the emitter lens 3 may have a convex shape, and in some embodiments, may be a hemisphere. By situating the UV-LED 2 at a focus of the emitter lens 3, light emitted by the UV-LED 2 may have its rays collimated into a parallel beam of light, shown as beam 12. The emitter lens 3 may further be situated and oriented so as to generate the beam 12 in a manner where the trajectories of light rays of beam 12 lie parallel to the long axis (Z-axis) of the chamber 122 (also referred to as an optical cuvette).

As further shown in FIG. 2B, the apparatus 120 may include a first window, shown as window 4, where the window 4 is transparent to UV radiation, in particular, at wavelengths above 250 nm. A suitable UV-transmitting material for use as window 4, for example, is quartz, where transmission for a 10 millimeter (mm) thick material may exceed 90% at 250 nm wavelength of light. The embodiments are not limited in this context. Similarly, apparatus 120 may include a second window, shown as window 8, where the second window is transparent to UV radiation at least above 250 nm wavelength, and may be composed of the same material as window 4. The chamber 112 may constitute a square cross-section tube, or a cylindrical tube that is capped at opposite ends using quartz windows (window 4 and window 8) and sealed by O-rings, on both ends.

In the embodiment of FIG. 2B, the detector 108 is shown as composed of a UV sensor 10, whose properties may be as described above, such as a solar-blind sensor. The detector 108 may further include a detector lens 9, where the detector lens 9 is disposed to intercept the beam 12, where the detector 108 is disposed at a second focus, that is, the focus of the detector lens 9. Notably, in other embodiments as in FIG. 2A, the detector 108 need not be disposed at the focus of a detector lens, and a detector lens need not be used at the detector 108. The use of a detector lens may enhance the amount of radiation detected, while the use of an emitter lens to generate a parallel beam may in some instances provide adequate radiation intensity to the detector 108 without need of a detector lens.

As further shown in FIG. 2B, the apparatus 120 may include a gas inlet 5 to conduct gas into the chamber 102, and a gas outlet 7 to conduct gas out of the chamber 102. In operation of the apparatus 120, gas containing ozone or other gas species to be measured may be provide through gas inlet 5, flowing through the chamber 102, and then out of chamber 102 through gas outlet 7. The UV-LED 2 may then be energized, generating radiation that enters the chamber 102 via emitter lens 3 and first window 4 as a parallel UV beam, shown as beam 12. The beam 12 represents light whose direction of propagation is from left to right as shown by the arrows. As beam 12 traverses the chamber as a beam of parallel light having a predetermined wavelength, such as approximately 260 nm, some photons of beam 12 may be absorbed by a target gas (not shown) to be measured, such as ozone, due to the optical absorption characteristics of the target gas. By the time the beam 12 reaches the detector 108, the intensity of beam 12 may be reduced from a first intensity at the point of entering the chamber 102, to a second intensity at the point of exiting the chamber 102, where the second intensity is less than the first intensity. Since the beam 12 is beam of parallel light, by careful arrangement of the components of emitter 104 and components of detector 108, a large fraction of all the light emitted from emitter 104 that is not otherwise absorbed by gas in the chamber 102 may be collected by the detector 108. This facilitates better determination of the concentration of a given target gas species that may be present in a given overall gas mixture provided to the chamber 102, based upon the detected light intensity of beam 12 at detector 108.

In particular embodiments, the ozone concentration of gas provided to chamber 102 may be determined in the following manner. The intensity of UV radiation (I) of the beam 12 after absorption of part of radiation by ozone may be expressed as:

$$I = I_o * \exp(-K * C_{oz}) \qquad \text{Eq. (2)},$$

where I is UV intensity after absorption, Io is UV intensity without absorption (without any ozone), $C_{oz}$ is ozone concentration, and K is a coefficient depending on wavelength and units used, and proportional to cuvette length, that is, the length of chamber 102. In other embodiments, the term $C_{oz}$ may be replaced with the general term "C" to stand for the concentration of any gas being measured according to the absorption of UV radiation.

The ozone concentration in the chamber 102 at a given instance may be calculated by the procedure described below. As an initial operation, a first automatic zeroing of readings of the apparatus 120 takes place. In the zeroing operation, the ozone concentration in the chamber 102 should be arranged to be zero. For the zeroing operation, when zero ozone concentration is present in the chamber 102, a controller of an analog to digital device (see amplifier/microcontroller 114) takes digital readings (Uo) of a signal intensity from an amplifier that amplifies a signal from the UV sensor 10. On the basis of the value of Uo the parameter N may be calculated according to:

$$N = \text{Ln}(U\text{max}/Uo) \qquad \text{Eq. (3),}$$

where Umax is maximal signal and Uo is the digital reading of a DAC at the moment of zeroing. Merely as an example, Umax may read 4.5 V, while Uo reads 3 V, without any ozone present. Then, intensity readings collected by apparatus 120 (which readings may be provided on a display) may be used to calculate C by:

$$C = (\text{Ln}(U\text{max}/U\text{av}) - N) * K \qquad \text{Eq. (4),}$$

where Uav is the average of actual digital readings of a DAC obtained during a given time. As an example, a sampling interval for taking the digital readings in the presence of ozone may be from 1 second to 20 seconds. The embodiments are not limited in this context. The number of digital readings may vary, while in one implementation a reading may be taken every 0.1 seconds, meaning a sample size for calculating Uav may range up to 100 readings or more. The embodiments are not limited in this context. Following the above example where UO is 3 V, the value of Uav may be 2.0 V, indicating the absorption of some of the radiation by the ozone. In some implementations, time of averaging may be installed in a program menu. K represents a calibrating coefficient (which may be installed in a program menu).

If ozone concentration is still zero and Uav is equal to Uo readings on the ozonometer will be equal to zero. In other cases where ozone is present in the chamber 102, readings will be proportional to the ozone concentration in chamber 102, and can be made equal to actual ozone concentration by changing of the coefficient K.

Because the intensity of UV light detected by the detector 108 is relatively high and stable, small differences in signal intensity may easily be discerned when ozone is present. In this manner, the apparatus 120 can measure small ozone concentration with a fast response time, facilitating use of the apparatus 120 in automatic control systems, where ozone concentration may be measured and is some cases controlled in real time.

Figure 2C:
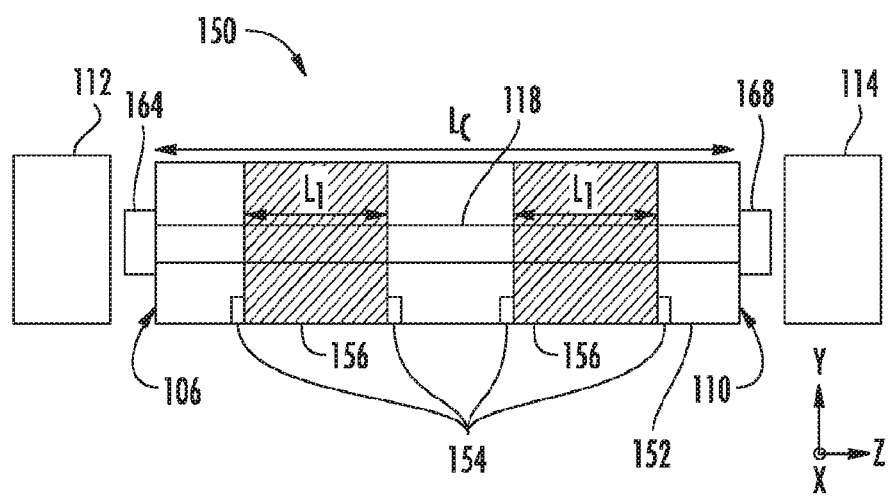
FIG. 2C depicts a side view of an additional apparatus according to various embodiments of the disclosure.

Turning now to FIG. 2C, there is shown another apparatus, apparatus 150, arranged according to further embodiments of the disclosure. The apparatus 150 may include similar components to those described above with respect to FIG. 2A and FIG. 2B. Gas inlets and outlets are omitted for clarity. The apparatus 150 differs from apparatus 100 in that an insert holder 154 is disposed in the chamber 152. The insert holder 154 may be arranged wherein at least one insert, shown as inserts 156, is reversibly fixable to the insert holder 154. The inserts 156 may comprise a UV-transmitting material, such as quartz, so that just a small percentage of the beam 118 is absorbed by the inserts 156. Notably, the insert holder 154 is shown merely schematically, and may represent any known structure for holding an object, such as slots, recesses, tabs, clips, springs, and the like. Moreover, the holder 154 may represent any number of objects for holding any number of inserts.

When in place in the chamber 152, the inserts 156 reduce the path length of gas through which the beam 118 travels between emitter 104 and detector 108. As shown, the length of the chamber 152, shown as $L_C$ which is the distance between the inner surfaces of the windows 4 and 8. Absent inserts 156 in the chamber 152, the beam 118 travels through a path length where gas is present equivalent to $L_C$ between emitter 104 and detector 108. When present, the inserts 156 reduce the path length of gas through which the beam 118 travels between emitter 104 and detector 108 by an amount equal to the total length of the inserts 156 along the long axis of the chamber 152 (Z-axis), in this example, by an amount equal to $2(L_I)$, where $L_I$ is the length of an insert as shown. By appropriate choice of the total length of the inserts, the path length of the beam 118 containing a gaseous species may be reduced by 50%, 75%, 90%, or 99% with respect to an empty chamber, for example. The embodiments are not limited in this context. Notably, the illustration may not be drawn to scale. For example, in some embodiments the insert(s) 156 may occupy nearly all of the path length of gas as compared to a chamber 152 without inserts. In particular examples the total gas path length, equivalent to $L_C - L_{Itot}$, where $L_{Itot}$ equals the total path through which beam 118 travels within the inserts 156 while traversing between the inner surfaces of windows 4 and 8, may equal as little 1 mm to 2 mm, and in some examples as little as 0.2 mm to 1 mm. This small path length of gas may readily and accurately be provided by use of machined quartz inserts that are insertable into a cuvette having quartz windows at either end as described above. This reduction of path length renders the apparatus 150 especially useful for measuring high concentrations of a gas species, such as ozone, where the reduction of the signal of beam 118 by absorption from ozone may be unacceptably high when the beam 118 reaches detector 108 after traveling the distance $L_C$ through a gas without the presence of inserts 156. On the other hand, the apparatus 150 provide a convenient configuration to also measure relatively lower concentrations of ozone, where the inserts 156 may be removed in the latter circumstance.

According to various embodiments, at the high ozone concentration range of measurement, concentrations of approximately 30 g/m$^3$ to 300 g/m$^3$ may readily be measured using inserts 156. At the low ozone concentration range, with inserts 156 removed from chamber 152, concentrations below 30 g/m$^3$ may be measured.

Notably, the emitter 164 and detector 168 of apparatus 150 need not include the optics of the embodiments of FIG. 2A and FIG. 2B, where the emitter acts as a point source generating a parallel light beam between emitter 164 and detector 168. An advantage of providing removable inserts to reduce the path length of a beam through a gas, is that the attenuation of light by a concentrated gas species may be maintained at an acceptable level, even if the light directed to the detector 168 is not a parallel beam of light.

Figure 2D:
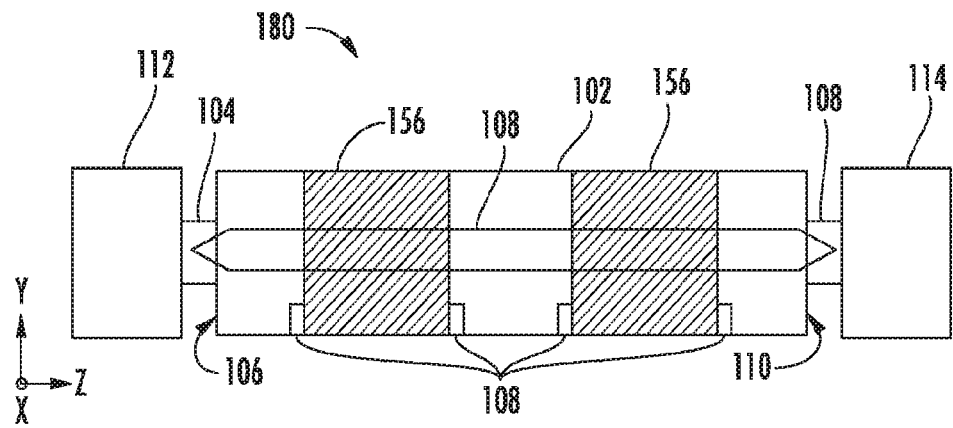
FIG. 2D depicts a side view of a further apparatus according to various embodiments of the disclosure.
Figure 2E:
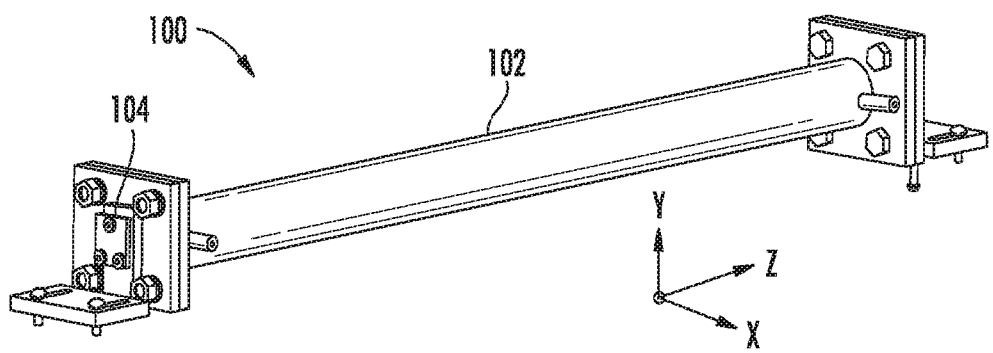
FIG. 2E depicts a perspective view of a variant of the apparatus of FIG. 2A.

Turning now to FIG. 2D there is shown an apparatus 180, arranged with the components as generally described above with respect to FIGS. 2A-2C. In this configuration, the emitter 104 and detector 108 may include the components as shown in FIG. 2B, providing a parallel beam of light between emitter 104 and detector 108, where a UV-LED is located at a focus of an emitter lens as described above. The apparatus 180 may be useful both for detection of small concentrations of ozone as well as large concentrations of ozone, where the inserts 156 are removable.

Figure 2F:
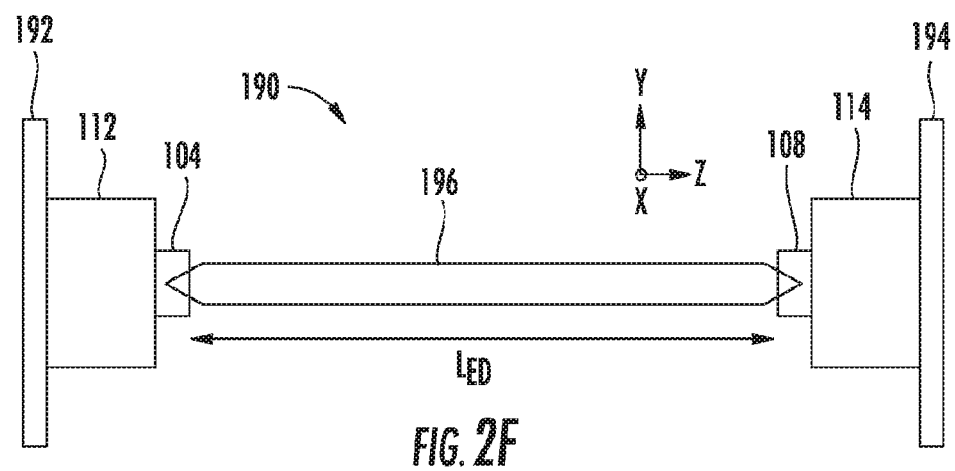
FIG. 2F depicts a side view of another apparatus according to various additional embodiments of the disclosure.

Turning now to FIG. 2F there is shown an implementation of an apparatus 190 according to further embodiments of the disclosure. In this example, the apparatus 190 may generally include the emitter components and detector components as detailed with respect to the above embodiments. A difference in this embodiment, is that the bounded volume may be in the form of a room or other relatively large space, rather than being a discrete chamber. Thus, with the illustrated embodiment the emitter 104 and detector 108 can be independently movable with respect to one another over relatively large distances (e.g., on the order of meters, depending on the size of the room). For example, in FIG. 2F the emitter 104 may be arranged on a first wall 192 of a room, while the detector 108 is arranged on a second wall 194 of the room. The relative placement of the emitter 104 on wall 192 and placement of detector 108 on wall 194 and the optics of the emitter 104, including an emitter lens (not shown in FIG. 2F), may be aligned with the detector 108 so that the beam 196 is intercepted by the detector 108. This alignment may be aided by use of a laser or other convenient alignment device. Additionally, instead of a wall, the emitter 104, detector 108, or both, may be placed on other objects within, or otherwise associated with, a room. In this manner, the ozone concentration or other gas concentration within an environment such as a room may be conveniently measured. In some examples, because the emitter 108 provides a parallel beam of light, in the apparatus 190 the distance between emitter 104 and detector 108 may range up to 30 meters, providing a convenient method for measuring low concentrations of a gas within a large space that may be occupied by humans. The apparatus 190 provides the additional advantage of flexibility in the placement of an ozone or other gas detector within many different environments, in that the emitter 104 and detector 108 are not tethered to one another and may operate over a wide range of distances.

FIG. 3A depicts a variant of the emitter 104, according to an embodiment of the disclosure, while FIG. 3B depicts details of the geometry of the emitter of FIG. 3A. As shown, the emitter 104 may include a UV-LED 202, an emitter lens 204, an adjustment component 206, a substrate 208, spacer 210. Also shown in FIG. 3A is a window 212, where the window 212 may be a quartz window mountable on an end of a chamber, as described with respect to FIG. 2B, for example. As noted above, the UV-LED 202 may be designed to emit radiation of a target wavelength, such as the wavelength range of the absorption peak of ozone at approximately 260 nm. The UV-LED 202 may be surface mounted on a printed circuit board, as represented by the substrate 208.

As shown in FIG. 3A, the adjustment component 206 may be a set of bolts and nuts, or other fastening device that engages the substrate 208 and window 212. The spacer 210 may represent a set of spacers such as washers, where at least one washer may be inserted on a given bolt between the substrate 208 and window 212. As further shown in FIG. 3A, the emitter lens 204 may have a generally hemispherical shape and may be affixed within a cavity provided in the window 212. Because the emitter lens 204 is affixed to the window 212, while the UV-LED 202 is affixed to the substrate 202, the distance between the emitter lens 204 and UV-LED 202 may be adjusted by adjusting the spacing between substrate 208 and window 212. This adjustment of spacing may be accomplished by the choice of the thickness of spacer 210, as well as the number of spacers 210 to be arranged on a given adjustment component, such as a bolt. Turning now to FIG. 3B, there is shown the geometry of light emitted by UV-LED 202. The rays 216 that are emitted from the UV-LED 202 may form a cone that is received by the emitter lens 204. By proper adjustment of the spacing S along the Z-axis between the emitter lens 204 and UV-LED 202, the UV-LED 202 may be maintained just at the focus 216 of the emitter lens 204, ensuring that light emerging to the right from the emitter lens 204 forms a parallel beam 220.

FIG. 4 depicts a variant of the detector 108 according to an embodiment of the disclosure. In this example, the detector includes an optical sensor 302, which sensor may be mounted in a window 310, such as a quartz window mounted on an end of a chamber. The detector 108 may include a detector lens 304, where the detector lens 304 is arranged to collect a beam 312 of parallel light and to focus the beam 312, where the focus of the detector lens 304 may coincide with the position of a sensing element (not separately shown) of the optical sensor 302.

Figure 5:
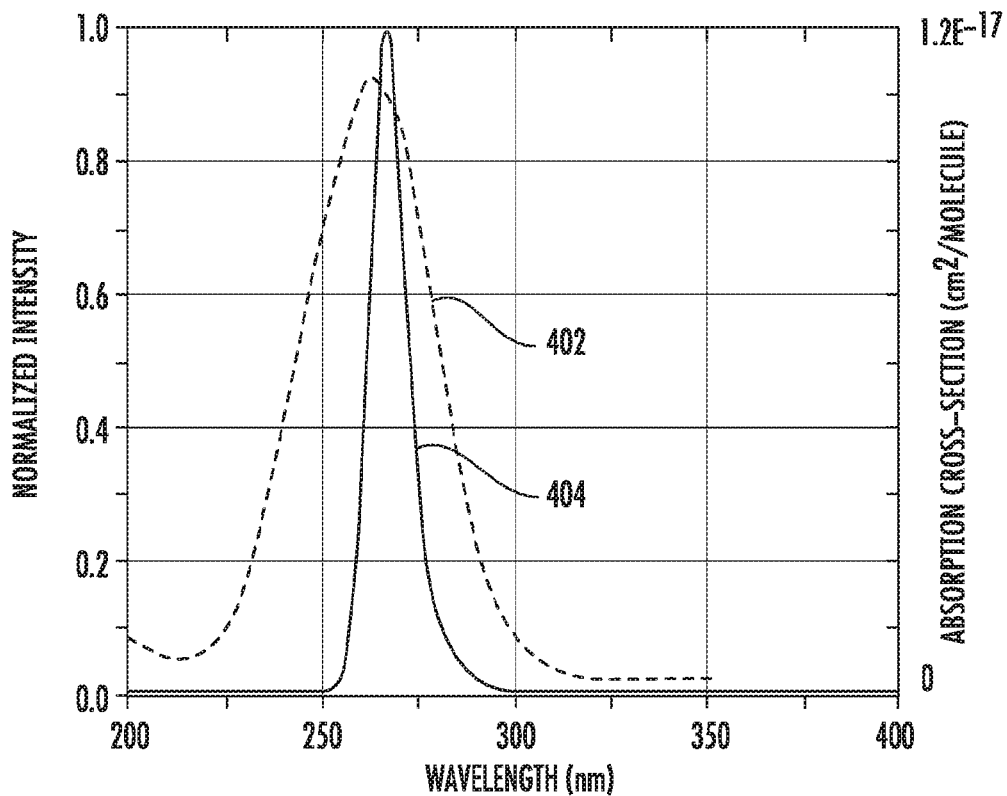
FIG. 5 is a composite graph depicting optical properties of ozone and an emitter, according to an embodiment of the disclosure.

To further illustrate the operating principles of an apparatus according to the present embodiments, FIG. 5 is a composite graph depicting optical properties of ozone and an emitter, according to an embodiment of the disclosure. In FIG. 5 a curve 402 illustrates an absorption peak for ozone, showing that the cross-section for absorption has a maximum at approximately 260 nm, while no absorption of light takes place above approximately 325 nm. Also shown is an emission spectrum of an exemplary UV-LED, shown as curve 404. The curve 404 is sharply peaked at approximately 265 nm, showing that nearly 100% of radiation of curve 404 overlaps with a wavelength range where the absorption of light by ozone molecules is high.

Figure 6:
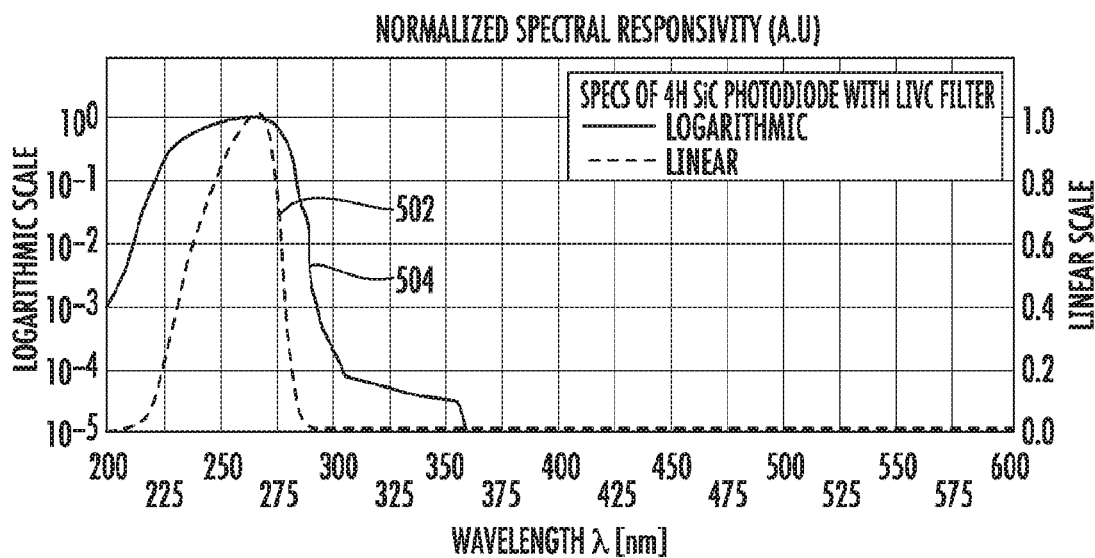
FIG. 6 is graph depicting optical properties of a detector according to an embodiment of the disclosure.

To further illustrate principles of detection, FIG. 6 is graph depicting optical properties of a detector according to an embodiment of the disclosure. In FIG. 6, the same data of silicon carbide photodiode with a radiation filter is shown as two different curves, linear curve 502, and logarithmic curve 504. As shown, a peak in responsivity takes place at 270 nm, while little radiation is detected above 290 nm wavelength. Accordingly, the detector device providing the data of FIG. 6 is suitable to detect radiation generated by the emitter device providing the data of curve 404.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are in the tended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Thus, the claims set forth below should be construed in view of the full breadth and spirit of the present disclosure as described herein.

What is claimed is:

1. An apparatus, comprising:
an extraction cuvette having a liquid inlet and a liquid outlet and a gas inlet and a gas outlet;
an optical cuvette having a gas inlet and a gas outlet, the gas inlet coupled to the gas outlet of the extraction cuvette;
an emitter comprising an ultraviolet light emitting diode (UV-LED) and a convex lens such that the UV-LED is at a focus of the convex lens, the emitter being positionable on a first end of the optical cuvette, the optical cuvette configured to contain the gas received from the extraction cuvette; and
a detector comprising an ultraviolet light sensor (UV sensor) and being positionable on a second end of the optical cuvette, the second end being opposite the first end, wherein the UV-LED comprises a point source, and wherein the emitter generates a parallel beam of light;

wherein convex lens is movably coupled to the UV-LED, and wherein a position of the UV-LED is adjustable so as to be disposed at a first focus of the emitter lens to collimate rays emitted by the UV-LED into a parallel beam of light.

2. The apparatus of claim 1, wherein the UV-LED comprises an emitter generating radiation in the range of 250 nm to 270 nm.

3. The apparatus of claim 1, wherein the UV sensor comprises a solar blind UV photodiode.

4. The apparatus of claim 1, wherein the convex lens comprises a hemisphere.

5. The apparatus of claim 1, wherein the detector comprises a detector lens, the detector lens coupled to the UV sensor, wherein the UV sensor is disposed at a second focus of the detector lens.

6. The apparatus of claim 5, wherein the detector lens comprises a convex lens.

7. The apparatus of claim 1, wherein the gas inlet of the extraction cuvette is coupleable to a gas distributor within the extraction cuvette to provide the gas in the form of a plurality of bubbles in a liquid disposed in the extraction cuvette.

8. The apparatus of claim 7, further comprising a temperature sensor disposed in or on the extraction cuvette for monitoring a temperature of the liquid within the extraction cuvette.

9. The apparatus of claim 7, wherein the liquid outlet of the extraction cuvette is disposed in a bottom portion of the extraction cuvette, the liquid outlet being coupled to an output pipe or tube for directing the liquid to a drain connection positioned at a level associated with a water level in the extraction cuvette to thereby maintain a predetermined water level in the extraction cuvette.

10. The apparatus of claim 9, wherein the emitter and detector are independently movable with respect to each other so as to align the emitter and detector such that the UV-LED emits the light that can be captured by the detector.

11. An apparatus, comprising:
an extraction cuvette having a liquid inlet and a liquid outlet and a gas inlet and a gas outlet;
an optical cuvette having a gas inlet and a gas outlet, the gas inlet coupled to the gas outlet of the extraction cuvette;
an emitter, the emitter comprising an ultraviolet light emitting diode (UV-LED) and being disposed on a first end of the optical cuvette;
a detector, the detector comprising an ultraviolet light sensor (UV sensor) and being disposed on a second end of the optical cuvette, the second end being opposite the first end;
an insert holder disposed in the optical cuvette; and
at least one optical insert, wherein the at least one insert is reversibly fixable to the insert holder, and wherein the at least one insert comprises a UV-transmitting material;
wherein the emitter comprises an emitter lens, the emitter lens movably coupled to the UV-LED, wherein a position of the UV-LED is adjustable so as to be disposed at a first focus of the emitter lens to collimate rays emitted by the UV-LED into a parallel beam of light.

12. The apparatus of claim 11, wherein the UV-LED comprises an emitter generating radiation in the range of 250 nm to 270 nm.

13. The apparatus of claim 12, wherein the detector comprises a detector lens, the detector lens coupled to the UV sensor, wherein the UV sensor is disposed at a second focus of the detector lens.

14. The apparatus of claim 11, wherein the UV sensor comprises a solar blind UV photodiode.

15. The apparatus of claim 11, further comprising:
a first window disposed on the first end of the optical cuvette; and
a second window disposed on the second end of the optical cuvette, the first window and the second window comprising a UV-transmitting material.

16. The apparatus of claim 11, wherein the optical cuvette comprises a path length of gas traversed by a beam emitted by the UV-LED between the emitter and the detector, wherein the path length of gas is between 0.2 mm and 1 mm when the at least one insert is affixed to the insert holder.

17. An apparatus, comprising:
an extraction cuvette having a liquid inlet and a liquid outlet and a gas inlet and a gas outlet;
an optical cuvette having a gas inlet and a gas outlet, the gas inlet coupled to the gas outlet of the extraction cuvette;
an emitter, the emitter comprising:
an ultraviolet light emitting diode (UV-LED) and being disposed on a first end of the optical cuvette; and
an emitter lens, the emitter lens coupled to the UV-LED, wherein the UV-LED is disposed at a first focus of the emitter lens;
a detector, the detector comprising:
an ultraviolet light sensor (UV sensor) and being disposed on a second end of the optical cuvette, the second end being opposite the first end; and
a detector lens, the detector lens coupled to the UV sensor, wherein the UV sensor is disposed at a second focus of the detector lens;
an insert holder disposed in the optical cuvette; and
at least one optical insert, wherein the at least one optical insert is reversibly fixable to the insert holder, and wherein the at least one insert comprises a UV-transmitting material;
wherein the optical insert is selectable to reduce a path length of gas through which a light beam travels between the emitter and the detector within the cuvette.

18. The apparatus of claim 17, wherein the gas inlet of the extraction cuvette is coupleable to a gas distributor within the extraction cuvette to provide the gas in the form of a plurality of bubbles in a liquid disposed in the extraction cuvette;
the extraction cuvette further comprising a temperature sensor disposed in or on the extraction cuvette for monitoring a temperature of the liquid within the extraction cuvette; and
wherein the liquid outlet of the extraction cuvette is disposed in a bottom portion of the extraction cuvette, the liquid outlet being coupled to an output pipe or tube for directing the liquid to a drain connection positioned at a level associated with a water level in the extraction cuvette to thereby maintain a predetermined water level in the extraction cuvette.

* * * * *